(12) United States Patent
Guu et al.

(10) Patent No.: US 7,727,760 B2
(45) Date of Patent: Jun. 1, 2010

(54) CELL COLONIES DISSECTING AND TRANSPLANTING APPARATUS

(75) Inventors: Yeou-Bin Guu, Taichung (TW); Yu-Hsi Hsing, Taichung (TW); Wann-Hsin Chen, Hsinchu (TW); Lih-Tao Hsu, Luzhu Shiang (TW); Jinn-Fa Wu, Taichung (TW)

(73) Assignee: Industrial Technology Research Institute, Hsinchu (TW)

( * ) Notice: Subject to any disclaimer, the term of this patent is extended or adjusted under 35 U.S.C. 154(b) by 1078 days.

(21) Appl. No.: 11/317,701

(22) Filed: Dec. 23, 2005

(65) Prior Publication Data

US 2006/0141616 A1 Jun. 29, 2006

(51) Int. Cl.
*C12M 1/26* (2006.01)
*C12M 3/00* (2006.01)
*G01N 1/30* (2006.01)
*G01N 33/48* (2006.01)

(52) U.S. Cl. .................. 435/309.1; 435/40.52; 606/132
(58) Field of Classification Search .............. 435/309.1, 435/40.52, 30; 219/121.68; 71/309.1; D24/130; 83/919; 73/864.41; 436/63, 174; 422/63; 606/132
See application file for complete search history.

(56) References Cited

U.S. PATENT DOCUMENTS 4,989,614 A * 2/1991 Dejter et al. ................. 600/565
5,750,103 A * 5/1998 Cherksey .................. 424/93.21
6,248,114 B1 * 6/2001 Ysebaert ..................... 606/132
2002/0106626 A1 * 8/2002 Muraca ....................... 435/1.3
2004/0084426 A1 * 5/2004 Okada .................... 219/121.68
2004/0230215 A1 * 11/2004 Eriksson et al. ............. 606/180

* cited by examiner

*Primary Examiner*—William H Beisner
*Assistant Examiner*—Danielle Henkel
(74) *Attorney, Agent, or Firm*—Pro-Techtor Int'l Services; Ralph Willgohs

(57) ABSTRACT

A cell colonies dissecting and transplanting apparatus comprises: a base, a platform, a feeding mechanism having at least three axis feeding means, a movable holder, a cutting means, a transplanting means, and a CCD image capturing means. The platform having the CCD image capturing means therebottom is disposed onto the base, and on the platform is defined with the holder for receiving a plurality of loading trays, so as to the original cell colonies and a plurality of media boards of subculture can be placed on the loading trays of holder, the holder can displace from a first axis feeding means and a second axis feeding means of feeding mechanism to moveably align with a first axis and a second axis. In addition, the cutting means and the transplanting means respectively capable of vertically move along a third axis feeding means of feeding mechanism are arranged onto the base, wherein the cutting means is provided with an array of invertable blades, and the transplanting means is defined with a bent capture needle for capturing the cell masses, whereby enabling to use operational analysis of controller to precisely cut, capture and pickedly place the original cell colonies.

17 Claims, 8 Drawing Sheets

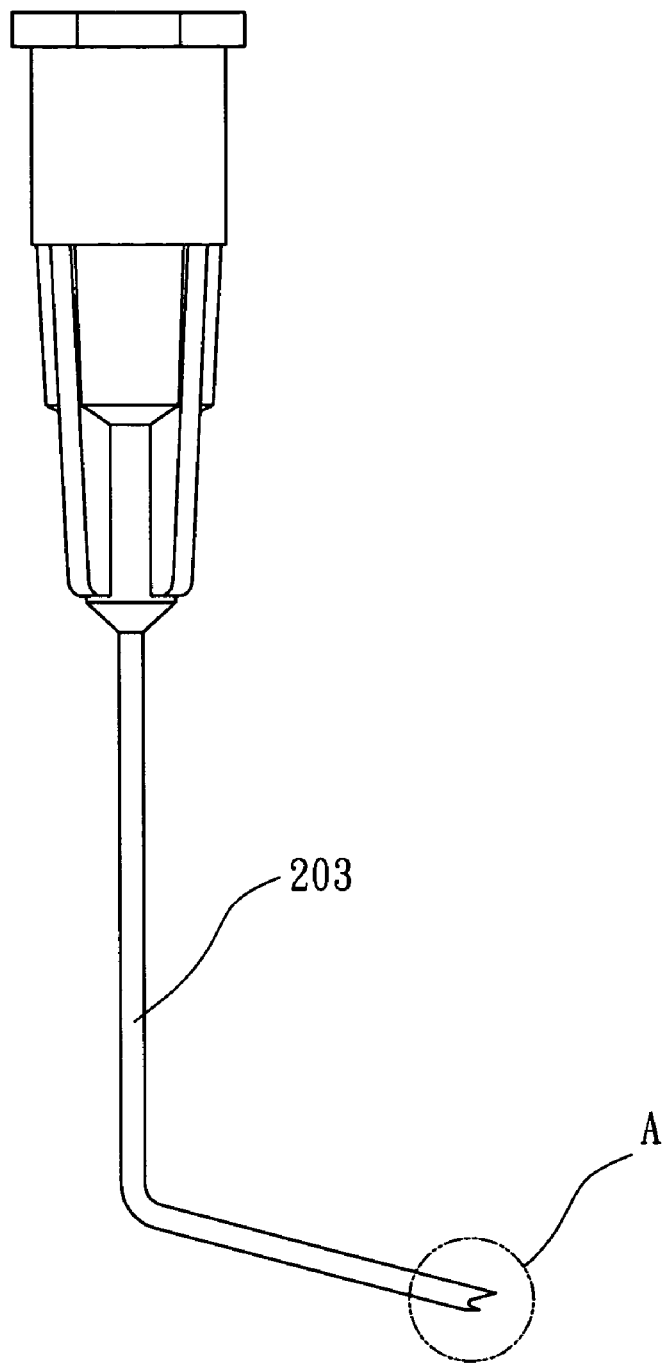
F I G . 7

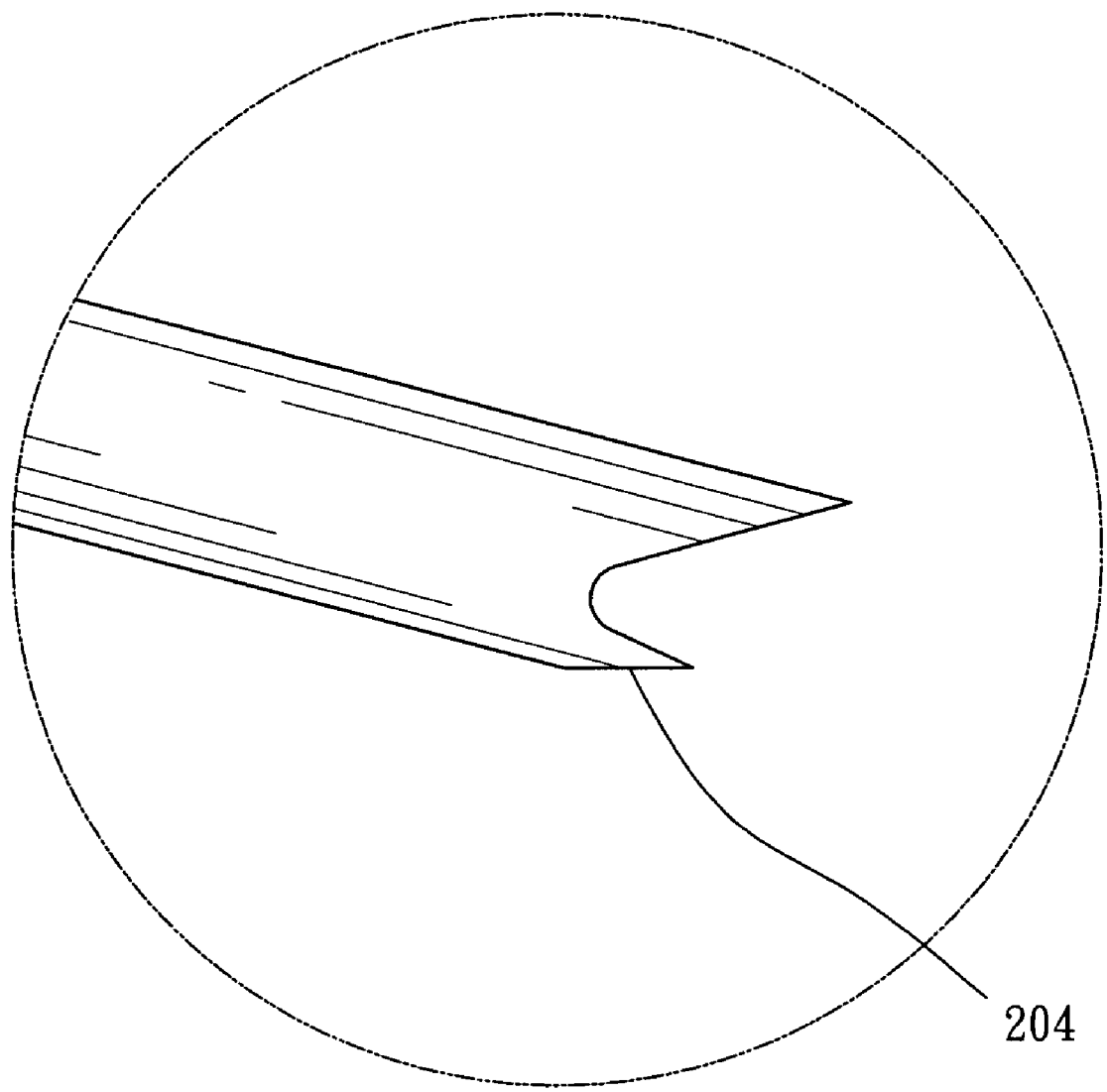
A
F I G . 8

CELL COLONIES DISSECTING AND TRANSPLANTING APPARATUS

BACKGROUND OF THE INVENTION

1. Field of the Invention

The present invention relates to a cell colonies dissecting and transplanting apparatus that can use automatization equipment to precisely cut, capture and pickedly place the original cell colonies, so as to decrease the infection probability.

2. Description of the Prior Arts

Nowadays, the molecular biotechnology is generally applied in human disease researches, especially in the human embryonic stem cells studyings. Hence, mass-produce of said human embryonic stem cells for medical usages is an indispensable study in the molecular biotechnology industry.

A conventional culturing method of human embryonic stem cells as shown in FIG. 1 comprises a plurality of original cell colonies 1 cultured on trophoblast cell of a media disk 2 for forming subculture. At this step, the biotechnology worker needs to dissect the reproduced cell colonies 1 by using a glass knife, and then pickedly places a plurality of undifferentiated cell masses 3 onto the trophoblast cell of a new media disk 4 for further culture. However, this conventional culturing method still has some defects, for example, the culturing space and production may be limited, and the cells may easy to be differentiated and infected.

The present invention has arisen to mitigate and/or obviate the afore-described disadvantages.

SUMMARY OF THE INVENTION

The primary objective of the present invention is to provide a cell colonies dissecting and transplanting apparatus, wherein a movable holder for receiving a plurality of loading trays is disposed onto a base and can displace from a first axis feeding drive and a second axis feeding drive to moveably align with a first axis and a second axis; in addition, a cutting assembly and a transplanting mechanism respectively capable of vertically move along two third axis feeding drive are arranged onto the base, wherein the cutting assembly is provided with an array of invertable blades, and the transplanting mechanism is defined with a bent capture needle for capturing the cell masses, whereby enabling to use the cutting assembly to dissect the original cell colonies into a plurality of cell masses, and then pickedly place said cell masses onto a plurality of media boards of subculture, while said cell colonies and the media boards of subculture are placed onto the loading trays of holder, so as to precisely cut, capture and pickedly place the cell colonies.

The secondary objective of the present invention is to provide a cell colonies dissecting and transplanting apparatus, wherein a platform having a image capturing device therebottom is disposed onto the base, by use of the holder, the original cell colonies and the media boards of subculture can be positioned relative to the image capturing device to capture their images, and then by using the operational analysis of controller, the cutting position of cutting assembly will be accurately modified to dissect the original cell colonies into a plurality cell masses, thereafter, said cell masses will be placed to the media boards of subculture such that the original cell colonies can be precisely cut, captured and pickedly placed.

The present invention will become more obvious from the following description when taken in connection with the accompanying drawings, which show, for purpose of illustrations only, a preferred embodiment in accordance with the present invention.

BRIEF DESCRIPTION OF THE DRAWINGS

FIG. 7 is a perspective view of a capture needle for the cell colonies dissecting and transplanting apparatus in accordance with the present invention;

FIG. 8 is an amplified view of a part of FIG. 7.

DETAILED DESCRIPTION OF THE PREFERRED EMBODIMENT

Figure 1:
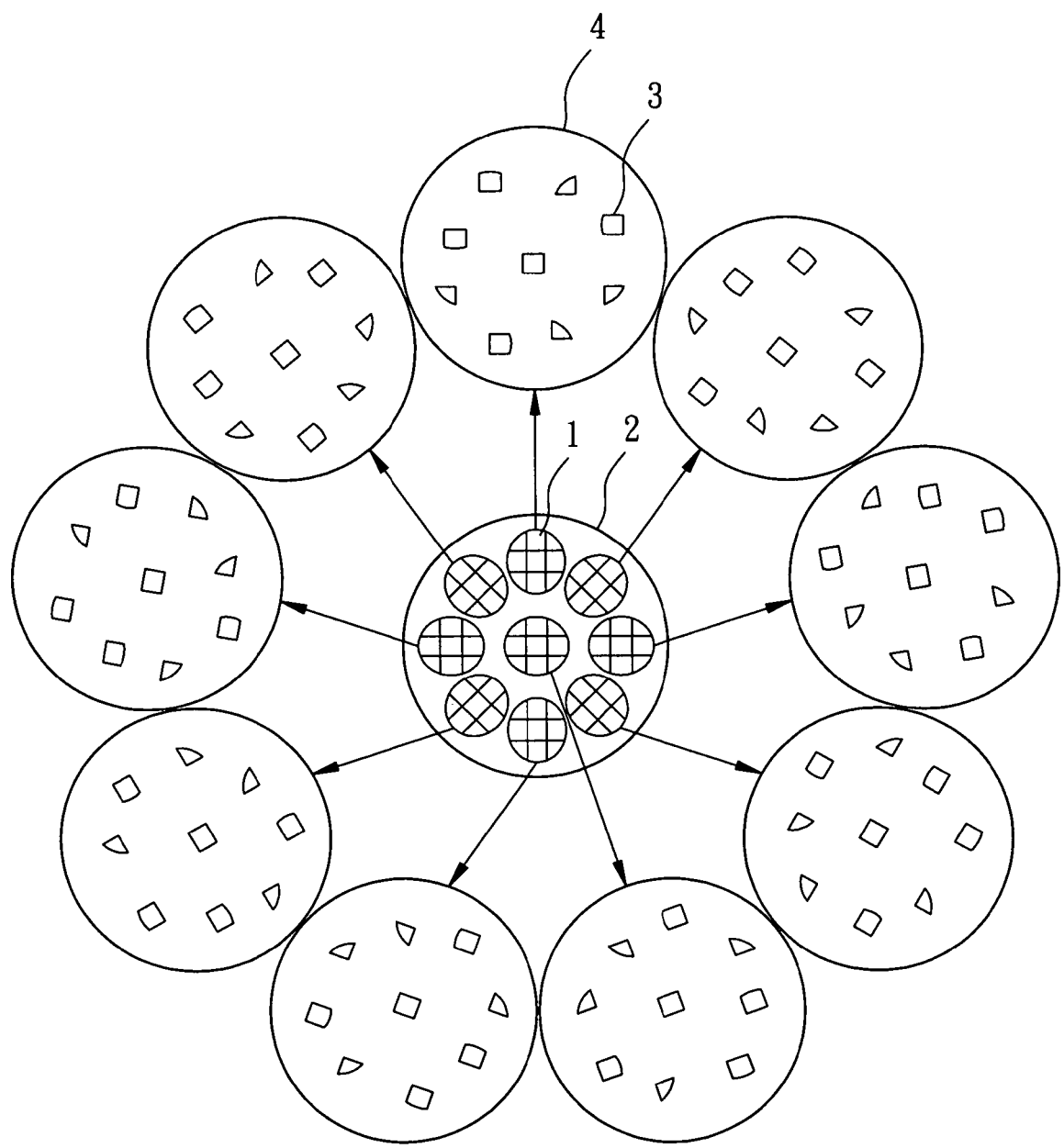
FIG. 1 is a perspective view of a conventional dissection and transplantation of cell colonies.
Figure 2:
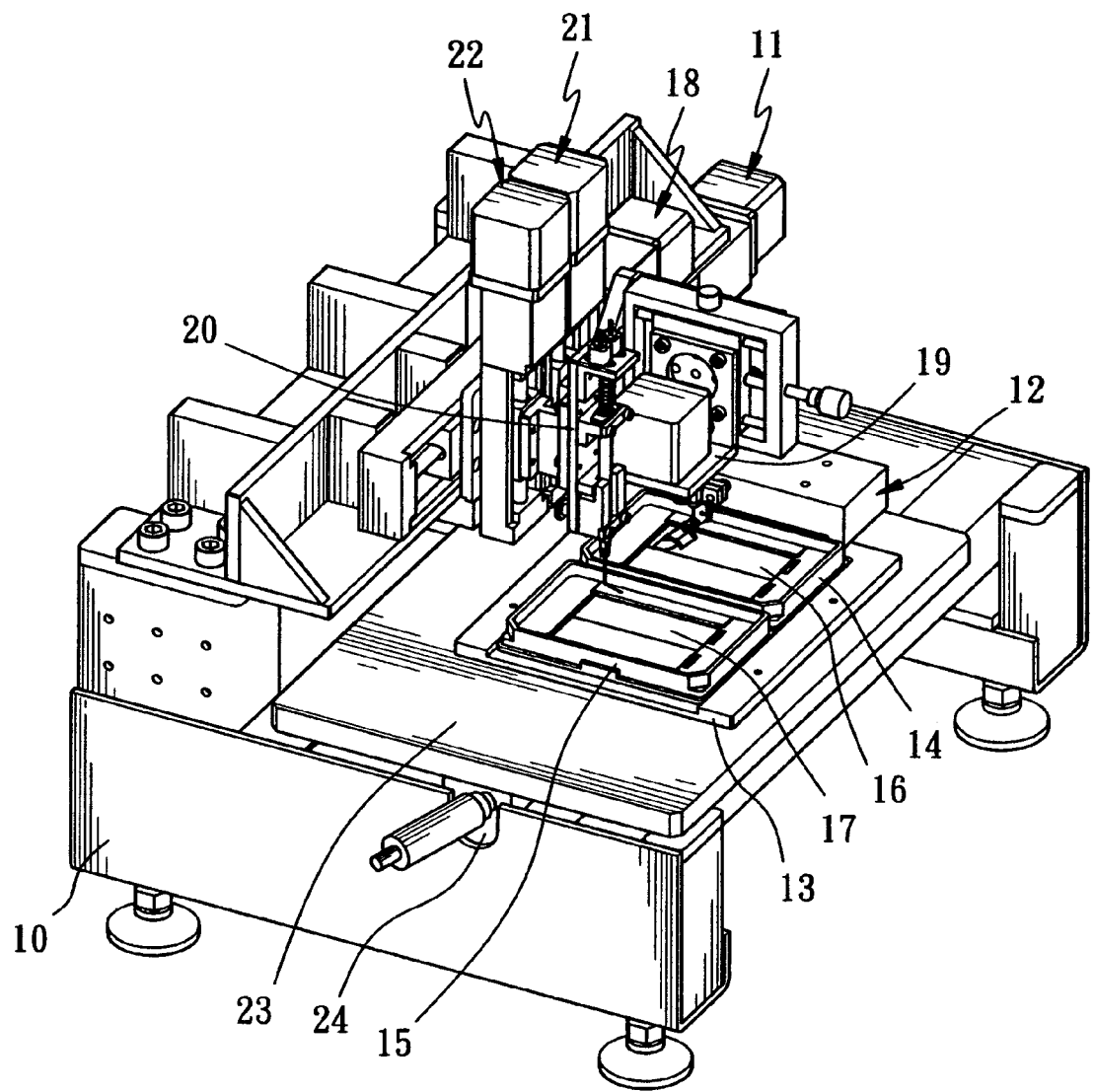
FIG. 2 is an exploded view of a cell colonies dissecting and transplanting apparatus in accordance with the present invention.

Referring to FIG. 2, a cell colonies dissecting and transplanting apparatus in accordance with the present invention is shown and comprises a base 10, two first axis (X-axis) feeding drives 11-18, a second axis (Y-axis) feeding drive 12, a movable holder 13, two loading trays 14-15, a plurality of media boards 16-17, a cutting assembly 19, a transplanting mechanism 20, two third axis feeding drives 21-22, an auxiliary platform 23.

By using the first axis (X-axis) feeding means 11 and the second axis (Y-axis) feeding means 12, the holder 13 can be couplingly driven on the base 10, so as to move in X-axis and Y-axis directions. The two loading trays 14-15 are respectively mounted onto the holder 13, wherein the loading tray 14 serves to receive the media boards 16 of cell colonies, while the loading tray 15 is applied to receive the media boards 17 of subculture. Moreover, by using the first axis (X-axis) feeding means 18, the cutting means 19 and the transplanting mechanism 20 both can be couplingly driven on the base 10, so as to cause a movement above the two loading trays 14-15 in X-axis direction. The cutting means 19 and the transplanting mechanism can also be respectively driven by means of two third axis (Z-axis) feeding drives 20-22, so as to cause a vertical movement above the two loading trays 14-15 in Z-axis direction. For the precision dissections of original cell colonies, the platform 23 having a image capturing device therebottom is arranged onto the base 10, and then by using the holder 13, the media boards 16 of original cell colonies can be pickedly placed onto the image capturing device, which in one embodiment is a CCD image capturing device, to cause an image capture, thereafter, by using operational analysis of controller, the cutting means 19 can be accurately moved onto the original cell colonies to cause a precision dissection through a vertical movement from above the colonies.

Figure 3:
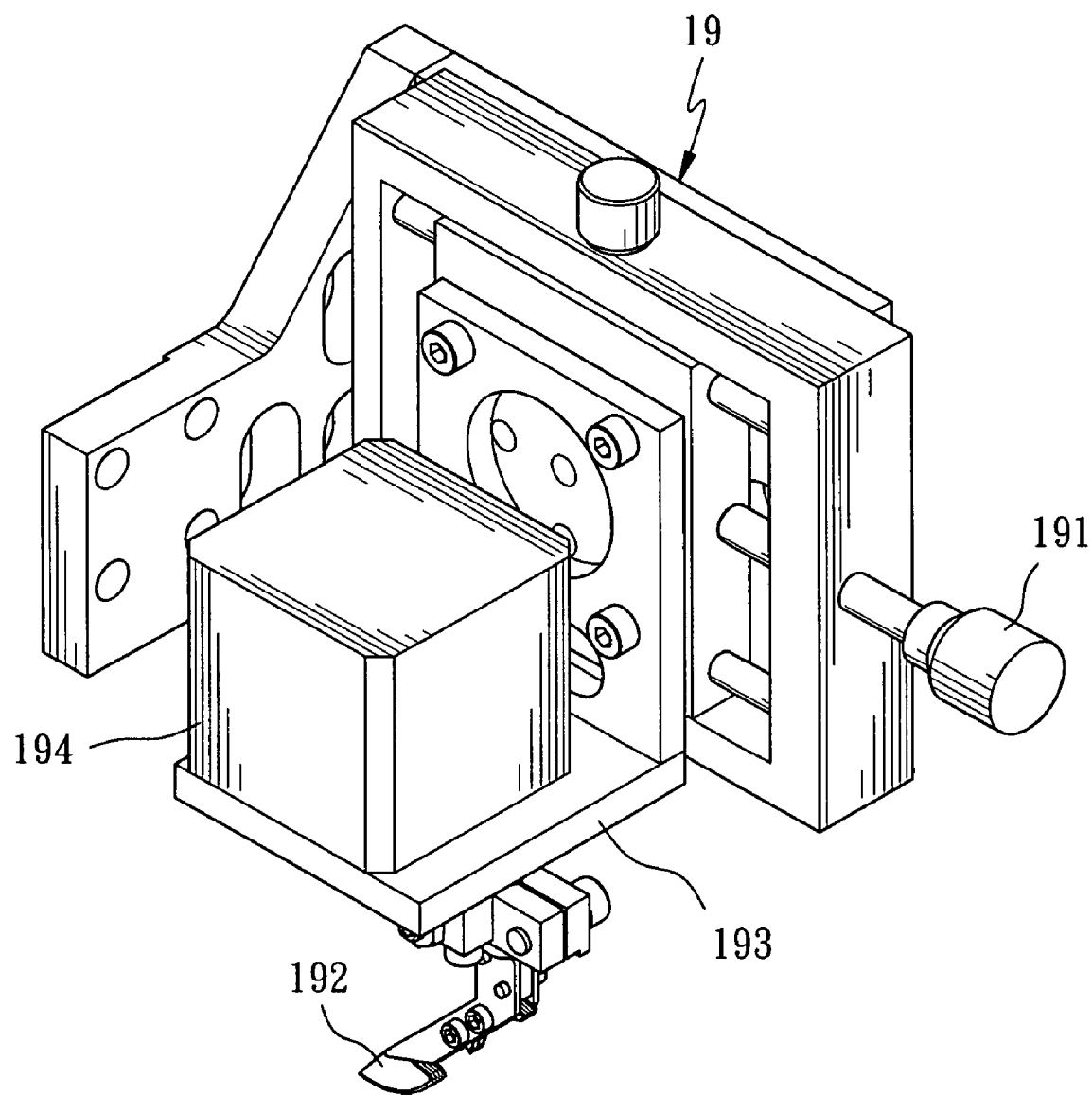
FIG. 3 is a perspective view of a cutting assembly for the cell colonies dissecting and transplanting apparatus in accordance with the present invention.
Figure 4:
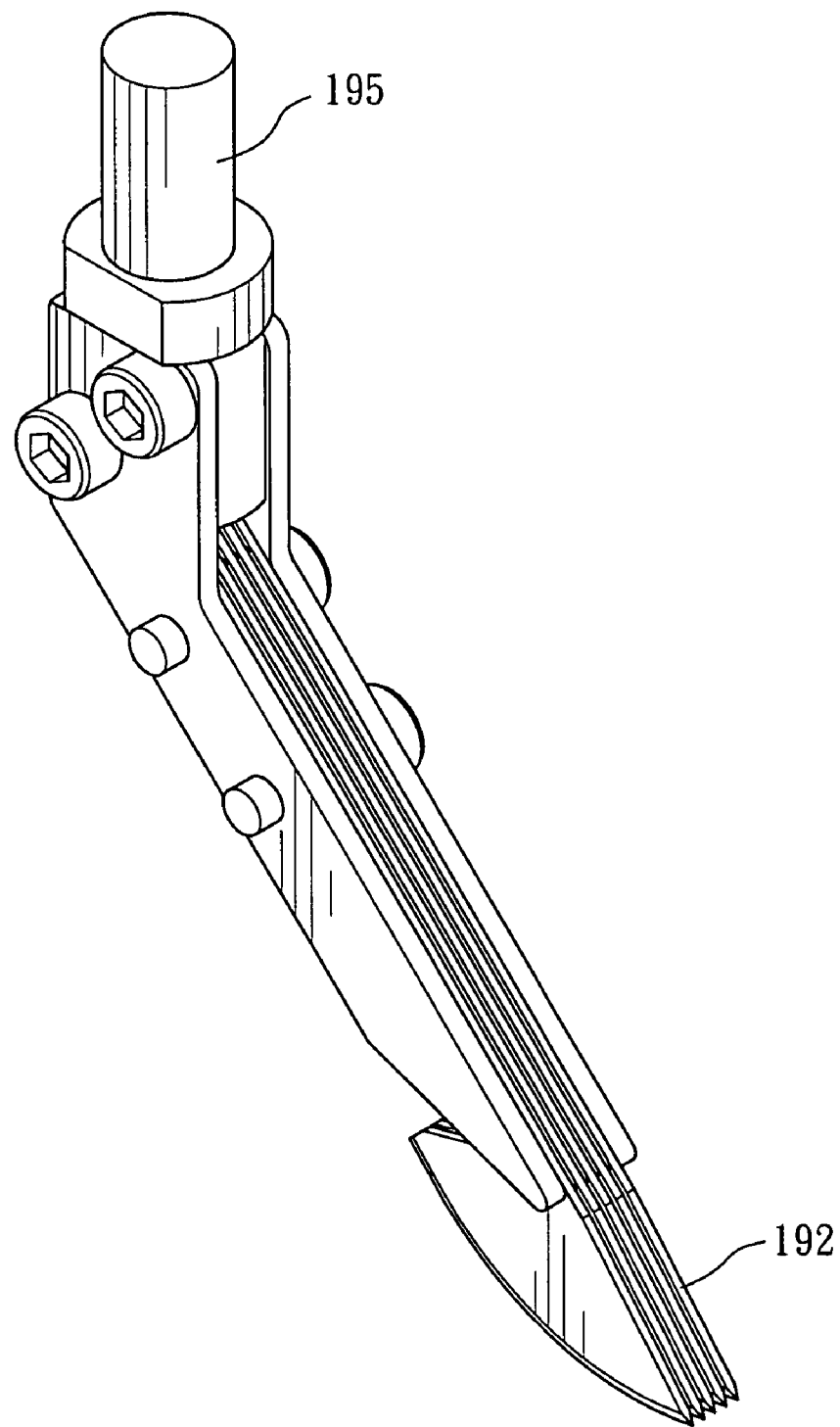
FIG. 4 is a perspective view of the array blades for the cell colonies dissecting and transplanting apparatus in accordance with the present invention.
Figure 5:
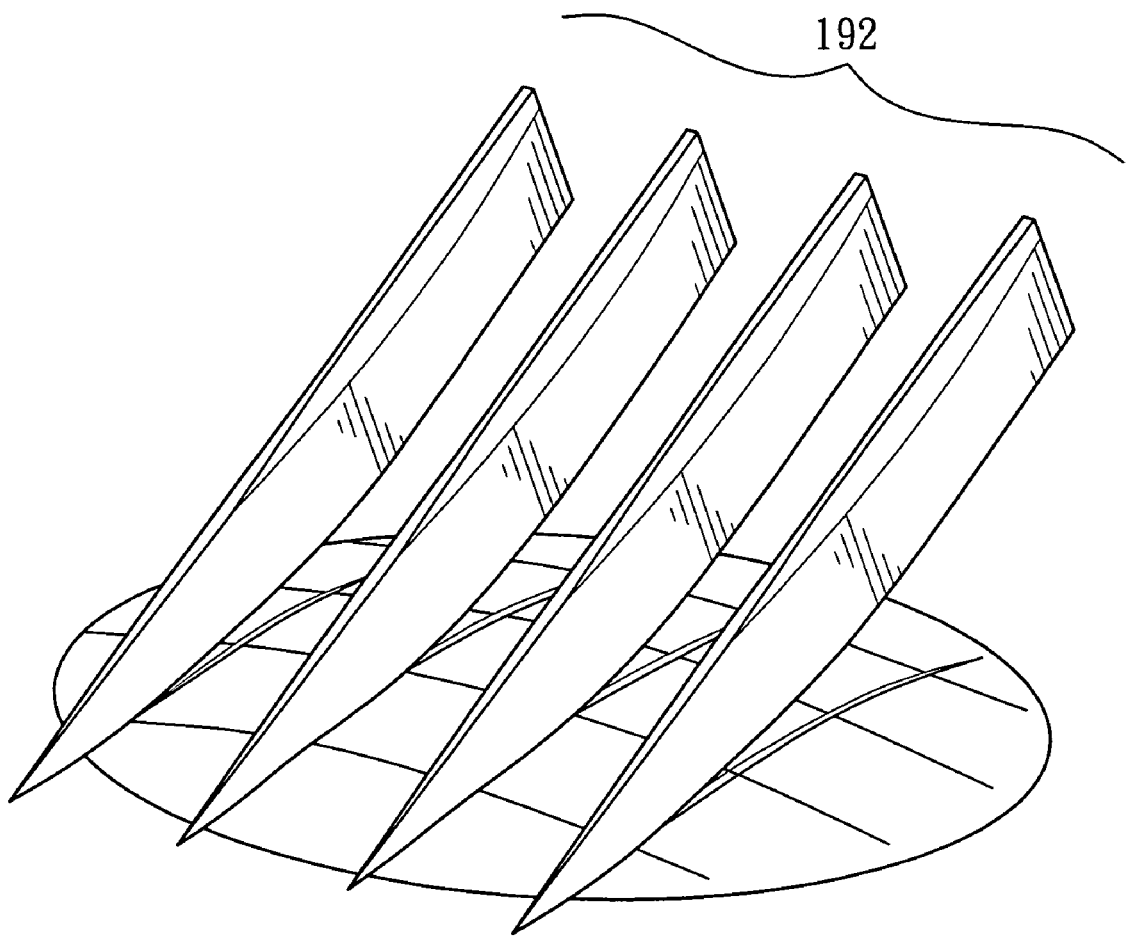
FIG. 5 is an operational view of the array blades for the cell colonies dissecting and transplanting apparatus in accordance with the present invention.

Referring to FIGS. 3 and 4, the cutting assembly 19 is provided with a fine tuning knob 191 in the Y-axis direction for causing the precision adjustment of a plurality of blades 192, and on a rack 193 is defined with a rotationally repositionable drive, such as a rotatable motor, 194 of which a shaft is coupled to a handle 195 of blades 192. By use of the rotation of motor 194, the cutting direction of blades 192 can be repositioned to 90 degree so as to across cut the original cell colonies. The blades 192 are respectively arranged in an array way to form a plurality of incisions, hence, as the blades 192 cut the original cell colonies at first time, the cell colonies (not shown) can be dissected into a plurality of small cell colonies (not shown). Referring next to FIG. 5, as the blades 192 further inverts to 90 degree to cut the dissected small cell colonies, said dissected small cell colonies will be divided into a plurality of array cell masses.

Figure 6:
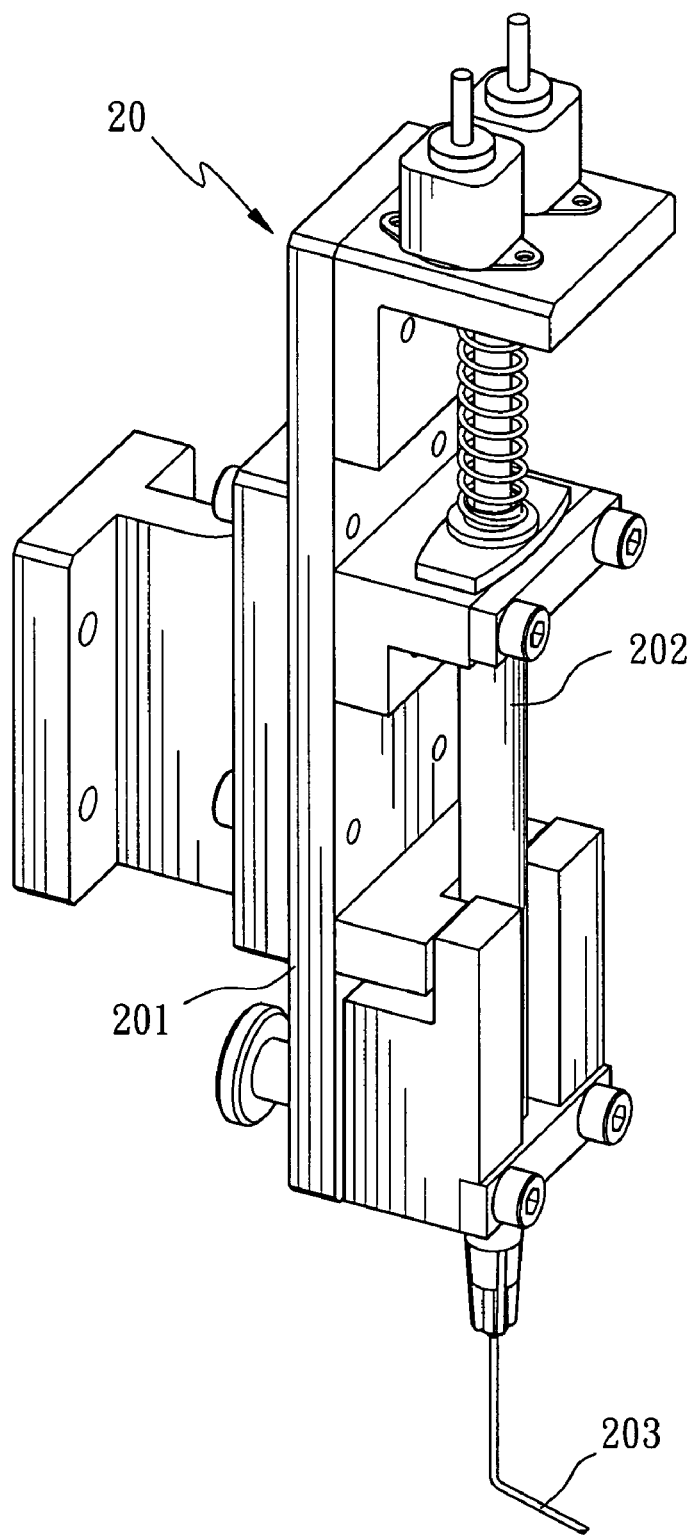
FIG. 6 is a perspective view of a transplanting mechanism for the cell colonies dissecting and transplanting apparatus in accordance with the present invention.

Referring to FIGS. 6-7, the transplanting mechanism 20 comprises a pneumatic barrel 202 fixed to an elongated plate 201, at the lower end of pneumatic barrel 202 is provided with a bent capture needle 203 for capturing the dissected cell masses, thus enabling the capture needle 203 to capture and pickedly place the dissected cell masses to the media boards 17 of substance, as the transplanting mechanism 20 moves downwardly. Thereafter, said cell masses will be releasably discharged in such a manner that the dissected cell masses can be respectively transplanted onto a plurality of media boards of subculture. Referring to the FIG. 8, one embodiment of the distal end of the captured needle 203 has a general u-shape profile, with protrusive tip 204 at the lower end of capture needle 203 for capturing and separating the dissected small cell masses from one another.

While we have shown and described various embodiments in accordance with the present invention, it should be clear to those skilled in the art that further embodiments may be made without departing from the scope of the present invention.

What is claimed is:

1. A cell colonies dissecting and transplanting apparatus comprising:
   a base;
   a feeding mechanism having at least three axis feeding drives being disposed onto the base;
   a holder for receiving at least one media board being mounted onto the base;
   an image capturing device mounted onto the base, and positionable for imaging the at least one media board;
   a cutting assembly provided with a plurality of blades fixed in a handle coupled onto the base for causing a linear motion relative to the holder, the plurality of blades being arranged so as to divide a substrate into a plurality of substantially linear subdivisions; and
   a transplanting mechanism defined with a bent capture needle, being arranged onto the base for causing a motion relative to the holder, a distal end of the capture needle is formed in a general u-shape with a protrusive lower tip for capturing and separating the dissected small cell masses from one another;
   wherein a rotationally repositionable drive provides an adjustable orientation of the cutting assembly relative to the at least one media board so as to subdivide a substrate in a pattern of intersecting gridlines.

2. The cell colonies dissecting and transplanting apparatus as claimed in claim 1, wherein the holder is designed to a moveable holder and can be couplingly driven by a plurality of axis feeding drives.

3. The cell colonies dissecting and transplanting apparatus as claimed in claim 1, wherein the holder is used to receive a plurality of loading trays, and on the loading trays are defined with a plurality of media boards of cell colonies and subculture.

4. The cell colonies dissecting and transplanting apparatus as claimed in claim 1, wherein the cutting assembly is couplingly driven by a plurality of axis feeding drives, and can cause a relative motion to the holder.

5. The cell colonies dissecting and transplanting apparatus as claimed in claim 1, wherein the blades of cutting assembly are driven to reposition 90 degrees by rotation of a motor so as to be positioned to cut across the original cell colonies.

6. The cell colonies dissecting and transplanting apparatus as claimed in claim 1, wherein the blades of cutting assembly are arranged in an parallel array.

7. The cell colonies dissecting and transplanting apparatus as claimed in claim 1, wherein the capture needle of the transplanting mechanism is coupled to a pneumatic barrel for capturing and releasably discharging the dissected small cell masses.

8. The cell colonies dissecting and transplanting apparatus as claimed in claim 1, wherein the distal end of the capture needle is formed in a general u-shape with a protrusive tip for capturing and separating the dissected small cell masses from one another.

9. A cell colonies dissecting and transplanting apparatus comprising:
   a base;
   a feeding mechanism having at least three axis feeding drives being disposed onto the base;
   a holder for receiving a plurality of media boards being mounted onto the base;
   a cutting assembly provided with a plurality of blades fixed in a handle coupled onto the base for causing a relative motion to the holder;
   a transplanting mechanism defined with a bent capture needle being arranged onto the base for causing a relative motion to the holder as well;
   a CCD image capture device for capturing the images of original cell colonies disposed onto the base, and by using the operational analysis of a controller, the cutting assembly will be controlled to accurately dissect the original cell colonies in a pattern of intersecting gridlines.

10. The cell colonies dissecting and transplanting apparatus as claimed in claim 9, wherein the holder is a moveable holder and can be couplingly driven by a plurality of axis feeding drives.

11. The cell colonies dissecting and transplanting apparatus as claimed in claim 9, wherein the holder is used to receive a plurality of loading trays, and on the loading trays are defined with a plurality of media boards of cell colonies and subculture.

12. The cell colonies dissecting and transplanting apparatus as claimed in claim 9, wherein the cutting assembly is positioned above the holder and couplingly driven by a plurality of axis feeding drives, and can cause a relative motion to the holder.

13. The cell colonies dissecting and transplanting apparatus as claimed in claim 9, wherein the blades of cutting assembly are driven to reposition by the rotation of a motor so as to cross-cut prior cell colonies subdivisions.

14. The cell colonies dissecting and transplanting apparatus as claimed in claim 9, wherein the blades of the cutting assembly are arranged in an array.

15. The cell colonies dissecting and transplanting apparatus as claimed in claim 9, wherein the capture needle of transplanting mechanism is coupled to a pneumatic barrel for capturing and releasably discharging the dissected small cell masses.

16. The cell colonies dissecting and transplanting apparatus as claimed in claim 9, wherein a distal end of the capture needle is formed in a general u-shape with a protrusive lower tip for capturing and separating the dissected small cell masses from one another.

17. The cell colonies dissecting and transplanting apparatus as claimed in claim 9, wherein a platform having a charge-coupled device (CCD) image capturing device therebottom is disposed onto the base for capturing the images of original cell colonies on the holder.

* * * * *